United States Patent [19]
Hölzemann et al.

[11] Patent Number: 5,215,966
[45] Date of Patent: Jun. 1, 1993

[54] PEPTIDE AND RENIN INHIBITORS

[75] Inventors: Günter Hölzemann, Seeheim; Peter Raddatz, Darmstadt; Claus J. Schmitges, Gross-Umstadt; Klaus Otto Minck, Ober-Ramstadt; Alfred Jonczyk, Darmstadt; Johannes Sombroek, Darmstadt; Joachim Gante, Darmstadt, all of Fed. Rep. of Germany

[73] Assignee: Merck Patent Gesellschaft mit Beschrankter Haftung, Darmstadt, Fed. Rep. of Germany

[21] Appl. No.: 126,060

[22] Filed: Nov. 27, 1987

[30] Foreign Application Priority Data

Nov. 27, 1986 [DE] Fed. Rep. of Germany ....... 3640535

[51] Int. Cl.$^5$ ..................... A61K 37/00; A61K 37/02
[52] U.S. Cl. ......................................... 514/18; 514/19; 530/330; 530/331; 530/800
[58] Field of Search ............... 530/329, 330, 331, 800; 514/16, 17, 18, 19

[56] References Cited

U.S. PATENT DOCUMENTS

| | | | |
|---|---|---|---|
| 4,725,580 | 2/1988 | Wagnon et al. | 514/17 |
| 4,746,643 | 5/1988 | Wagnon et al. | 514/17 |
| 4,755,592 | 7/1988 | Raddatz et al. | 530/323 |

FOREIGN PATENT DOCUMENTS

| | | | |
|---|---|---|---|
| 0077028 | 4/1963 | European Pat. Off. | |
| 0081783 | 6/1983 | European Pat. Off. | 530/331 |
| 0152255 | 8/1985 | European Pat. Off. | |
| 84/03044 | 8/1984 | PCT Int'l Appl. | |

OTHER PUBLICATIONS

Burger. *Medicinal Chemistry.* 1960, pp. 565–571, 578–581, 600–601.
Denkewalter et al. *Progress In Drug Research.* 1966, vol. 10, pp. 610–612.
Plattner et al. *J. Med. Chem.* 1988. 31(12). pp. 2277–2288.
Kokubu et al., Biochemical Pharmacology, vol. 22 pp. 3217–3223 (1973).
Giorgio Bolis et al., "Renin Inhibitors. Dipeptide Analogues of Angiotensinogen Incorporating Transistion-State, Nonpeptidic Replacements at the Scissile Bond"/J. Med. Chem. 1987m 30, 1729–1737.
Medicinal Chemistry, 3rd Ed. Part II. by Alfred Burger; Copyright 1970 by John Wiley & Sons.

Primary Examiner—Merrell C. Cashion, Jr.
Assistant Examiner—Bennett Celsa
Attorney, Agent, or Firm—Millen, White, Zelano & Branigan

[57] ABSTRACT

Novel amino acid derivatives of the formula I $$X-Z-NH-CHR^1-CO-NR^2-CHR^3-CR^4-(CHR^5)_n-CO-E-W'-Y$$

wherein X, Z, $R^1$, $R^2$, $R^3$, $R^4$, $R^5$, E, W', Y and n have the meanings defined herein and their salts inhibit the activity of human plasma renin.

13 Claims, No Drawings

PEPTIDE AND RENIN INHIBITORS

BACKGROUND OF THE INVENTION

The invention relates to novel amino acid derivatives. Similar compounds have been disclosed in EP-A-152,255.

SUMMARY OF THE INVENTION

It is an object of the invention to provide new compounds having valuable properties, in particular those which can be used for the preparation of medicaments.

Upon further study of the specification and appended claims, further objects and advantages of this invention will become apparent to those skilled in the art.

These objects have been achieved by providing new amino acid derivatives of the formula I

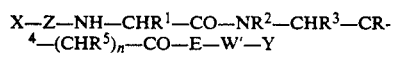

in which

X is H, $R-O-C_mH_{2m}-CO-$, $R-C_mH_{2m}-O-CO-$, $R-C_mH_{2m}-CO-$, $R-SO_2$, $(R-C_mH_{2m})-L(R-C_pH_{2p})-C_rH_{2r}-CO-$, $R-(NHCH_2CH_2)_mNHCH_2CO-$ or 9-fluorenyl-$C_mH_{2m}-O-CO-$, Z is 0 to 4 amino acid radicals which are connected to one another in a peptide fashion and which are selected from the group comprising Abu, Ada, Ala, Arg, Asn, Asp, Bia, Cal, Dab, Gln, Glu, His, N(im)-alkyl-His, Ile, Leu, tert.-Leu, Lys, Met, αNal, βNal, Nbg, Nle, Orn, Phe, Pro, Ser, Thr, Tic, Trp, Tyr and Val, E is 0 to 2 amino acid radicals which are connected to one another in a peptide fashion and which are selected from the group comprising Abu, Ala, Cal, His, Ile, Leu, Met, Nle, Phe, Trp, Tyr and Val, W' is absent or is $-NH-CHR^6-CR^7-(CHR^8)_n-CO-$ Y is $-Q-C_tH_{2t}-R^9$ or $NA_2$, W'—Y is alternatively

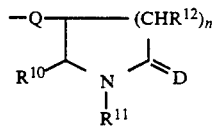

L is CH or N,
Q is O or $NR^{13}$,
D is O or S,
$R^1$ is pyridylmethyl or piperidylmethyl,
R, $R^3$, $R^6$,
$R^9$ and $R^{10}$ are in each case H, A, Ar, Ar-alkyl, Het, Het-alkyl, or cycloalkyl having 3-7C atoms, cycloalkylalkyl having 4-11 C atoms, bicycloalkyl or tricycloalkyl in each case having 7-14C atoms, bicycloalkylalkyl or tricycloalkylalkyl in each case having 8-18 C atoms which is in each case unsubstituted or monosubstituted or polysubstituted by A, AO and/or Hal,
$R^2$, $R^5$, $R^8$, $R^{11}$,
$R^{12}$ and $R^{13}$ are in each case H or A,
$R^4$ and $R^7$ are in each case (H, OH), (H, $NH_2$) or =0,
m, p, r and t are in each case 0, 1, 2, 3, 4 or 5,
n is 1 or 2, Ar is phenyl which is unsubstituted, or monosubstituted or polysubstituted by A, AO, Hal, $CF_3$, OH and/or $NH_2$, unsubstituted naphthyl or unsubstituted pyridyl, Het is a saturated or unsaturated 5- or 6-membered heterocyclic radical which has 1-4 N, O and/or S atoms and which is condensed with a benzene ring or a pyridine ring and/or may be monosubstituted or polysubstituted by A, AO, Hal, $CF_3$, HO, $O_2N$, carbonyl oxygen, $H_2N$, HAN, $A_2N$, AcNH, AS, ASO, $ASO_2$, AOOC, CN, $H_2NCO$, ANHCO, $A_2NCO$, ArNHCO, Ar-alkyl-NHCO, $H_2NSO_2$, $ASO_2NH$, Ar, Ar-alkyl, Ar-alkenyl, hydroxyalkyl and/or aminoalkyl in each case having 1-8 C atoms, and/or whose N and/or S heteroatoms may also be oxidized, Hal is F, Cl, Br or I, Ac is $H-CO-$, $A-CO-$, $Ar-CO-$, $A-NH-CO-$ or $Ar-NH-CO-$, and A is alkyl having 1-8 C atoms, furthermore in which one or more $-NA-CO-$ groups may be in the place of one or more $-NH-CO-$ groups, but in which the E and W' groups may not simultaneously be absent, and the salts thereof.

In the foregoing, selection of variables defined together is made independently.

It has been found that the compounds of the formula I, and their salts, have very valuable properties. Above all, they inhibit the activity of human plasma renin. This action can be detected, for example, using the method of F. Fyhrquist et al., Clin. Chem. 22, 250 256 (1976). It is notable that these compounds are very specific inhibitors of renin; for the inhibition of other aspartyl-proteinases (for example pepsin and kathepsin D), significantly higher concentrations of these compounds are generally necessary, e.g., concentrations about 100 to 1000 times as high.

The compounds can be employed as active ingredients in medicaments in human and veterinary medicine, in particular for prophylaxis and treatment of coronary, circulatory and vascular disorders, above all hypertonia, cardiac insufficiency and hyperaldosteronism. In addition, the compounds can be used for diagnostic purposes in order to determine the possible contribution of renin activity to maintenance of the pathological state in patients having hypertonia or hyperaldosteronism. Such diagnostic tests can be performed in the manner disclosed in EP-77,028.

The above- and below mentioned abbreviations of amino acid radicals represent the radicals $-NH-CHR-CO-$ (in which R has the specific meaning known for each amino acid) of the following amino acids:

| | |
|---|---|
| Abu | 2-aminobutyric acid |
| Ada | adamantylalanine |
| Ala | alanine |
| Asn | asparagine |
| Asp | aspartic acid |
| Bia | benzimidazolylalanine |
| Cal | cyclohexylalanine |
| Dab | 2,4-diaminobutyric acid |
| Gln | glutamine |
| Glu | glutamic acid |
| His | histidine |
| N(im)-alkyl-His | histidine which is substituted in the 1-position of the imidazole ring by A |
| Ile | isoleucine |
| Leu | leucine |
| tert.-Leu | tert.-leucine |
| Lys | lysine |

| | |
|---|---|
| Met | methionine |
| αNal | α-naphthylalanine |
| βNal | β-naphthylalanine |
| Nbg | (2-norbornyl)-glycine |
| Nle | norleucine |
| N-Me-His | N-methyl-histidine |
| N-Me-Phe | N-methyl-phenylalanine |
| Orn | ornithine |
| Phe | phenylalanine |
| Pia | 3-(piperidyl)-alanine, e.g. 2-Pia = 3-(2-piperidyl)-alanine |
| Pro | proline |
| Pya | 3-(pyridyl)-alanine, e.g. 3-Pya = 3-(3-pyridyl)-alanine |
| Ser | serine |
| Thr | threonine |
| Tic | tetrahydroisoquinoline-1-carboxylic acid |
| Trp | tryptophan |
| Tyr | tyrosine |
| Val | valine. |

Furthermore, the following terms have the following meanings:

| | |
|---|---|
| BOC | tert.-butoxycarbonyl |
| imi-BOM | benzyloxymethyl in the 1-position of the imidazole ring |
| CBZ | benzyloxycarbonyl |
| DNP | 2,4-dinitrophenyl |
| imi-DNP | 2,4-dinitrophenyl in the 1-position of the imidazole ring |
| ETNC | N-ethylcarbamoyl |
| ETOC | ethoxycarbonyl |
| FMOC | 9-fluorenylmethoxycarbonyl |
| IPNC | N-isopropylcarbamoyl |
| IPOC | isopropoxycarbonyl |
| MC | morpholinocarbonyl |
| OMe | methyl ester |
| OEt | ethyl ester |
| PBB | 4-phenyl-2-benzylbutyryl |
| POA | phenoxyacetyl |
| DCCI | dicyclohexylcarbodiimide |
| HOBt | 1-hydroxybenzotriazole. |

In cases where it is possible for the above-mentioned amino acids to occur in several enantiomeric forms, all these forms and also mixtures thereof (for example the DL forms) are included above and below, for example as part of the compounds of the formula I. The L forms are preferred. Where individual compounds are listed below, the abbreviations for these amino acids in each case relate to the L form, unless expressly stated otherwise.

The radicals or parameters X, Z, E, W', Y, L, Q, D, R, $R^1$ to $R^{12}$, m, n, p, r, t, Ar, Het, Hal, Ac, A, $G^1$, $G^2$, $E^1$, $E^2$, $Z^1$ $Z^2$, and W above and below have the meanings specified in the formula I, II or III, unless expressly stated otherwise. If two radicals R are present in a compound of the formula I, they may be identical to or different from one another.

In the formulae above, A has 1–8, preferably 1, 2, 3 or 4 carbon atoms. A is preferably methyl, furthermore ethyl, propyl, isopropyl, butyl, isobutyl, sec.-butyl or tert.-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl.

Typically, all alkyl portions mentioned above have up to 8 carbon atoms, including, for example, the alkenyl and alkyl portions of Ar-alkenyl, Ar-alkyl, Ar-alkyl-NHCO, hydroxyalkyl and aminoalkyl.

Cycloalkyl is preferably cyclopropyl, cyclobutyl, cyclopentyl, cyclohexyl or cycloheptyl, but alternatively, for example, 1-, 2- or 3-methylcyclopentyl, or 1-, 2-, 3- or 4-methylcyclohexyl.

Accordingly, cycloalkyl-alkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl, but alternatively, for example, 1-, 2- or 3-methylcyclopentylmethyl, or 1-, 2-, 3- or 4-methylcyclohexylmethyl.

Bicycloalkyl is preferably 1- or 2-decalyl, 2-bicyclo[2,2,1]heptyl or 6,6-dimethyl-1-bicyclo[3,1,1]heptyl.

Tricycloalkyl is preferably 2-adamantyl.

Hal is preferably F, Cl or Br, but alternatively I.

Ac is preferably H—CO—, A—CO—, such as acetyl, propionyl or butyryl, Ar—CO—, such as benzoyl, o-, m- or p-methoxybenzoyl or 3,4-dimethoxybenzoyl, A—NH—CO—, such as N-methyl- or N-ethylcarbamoyl, or Ar—NH—CO, such as N-phenylcarbonyl.

Ar is preferably phenyl, furthermore preferably o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, o-, m- or p-hydroxyphenyl, 2,3-, 2,4-, 2,5-, 2,6-, 3,4- or 3,5-dimethoxyphenyl, 3,4,5-trimethoxyphenyl, o-, m- or p-aminophenyl, or 1- or 2-naphthyl.

Accordingly, Ar-alkyl is preferably benzyl, 1-or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxybenzyl, 1- or 2-o-, -m- or -p-methoxyphenylethyl, o-, m- or p-fluorobenzyl, 1- or 2-o-, -m- or -p-fluorophenylethyl, o-, m- or p-chlorobenzyl, 1- or 2-o-, -m- or -p-chlorophenylethyl, o-, m- or p-bromobenzyl, 1- or 2-o-, -m- or -p-bromophenylethyl, o-, m- or p-iodobenzyl, 1- or 2o-, -m- or -p-iodophenylethyl, o-, m- or p-trifluoromethylbenzyl, o-, m- or p-hydroxybenzyl, 2,3-, 2,4-, 2,5-, 2,6-, 3,4- or 3,5-dimethoxybenzyl, 3,4,5-trimethoxybenzyl, o-, m- or p-aminobenzyl, or 1- or 2-naphthylmethyl.

Het is preferably 2- or 3-furyl, 2- or 3-thienyl, 1-, 2-or 3-pyrryl, 1-, 2-, 4- or 5-imidazolyl, 1-, 3-, 4-or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3-or 4-pyridyl, 2-, 4-, 5- or 6-pyrimidyl, furthermore preferably 1,2,3-triazol-1-, -4- or -5-yl, 1,2,4-triazol -1, -3- or -5-yl, 1- or 5-tetrazolyl, 1,2,3-oxadiazol -4- or -5-yl, 1,2,4-oxadiazol-3- or -5-yl, 1,3,4-thiadiazol -2-or -5-yl, 1,2,4-thiadiazol-3- or -5-yl, 2,1,5-thiadiazol-3- or -4-yl, 2-, 3-, 4-, 5- or 6-2H-thiopyranyl, 2-, 3-or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolyl, or 2-, 4-, 5-, 6-, 7-or 8-quinazolyl. The heterocyclic radicals may also be partly or completely hydrogenated. Het can thus also be, for example, 2,3-dihydro-2-, -3-, -4- or -5-furyl, 2,5-dihydro-2-, -3-, -4- or -5-furyl, tetrahydro-2- or -3-furyl, tetrahydro-2- or -3-thienyl, 2,3-dihydro-1-, -2-, -3-, -4- or -5-pyrryl, 2,5-dihydro-1-, -2-, -3-, -4- or -5-pyrryl, 1-, 2- or 3-pyrrolidinyl, tetrahydro-1-, -2- or -4-imidazolyl, 2,3-dihydro-1-, -2-, -3-, -4- or -5-pyrazolyl, 2,5-dihydro-1-, -2-, -3-, -4or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4or -5-pyrimidyl, 1-, 2- or 3-piperazinyl, 1,2,3,4-tetrahydro-1-, -2-, -3-, -4-, -5-, -6-, -7- or -8-quinolyl, or 1,2,3,4-tetrahydro-1-, -2-, -3-, -4-, -5-, -6-, -7- or -8-isoquinolyl.

The heterocyclic radicals may also be substituted as specified. Het may thus preferably also be: 2-amino-4-thiazolyl, 4-carboxy-2-thiazolyl, 4-carbamoyl-2-thiazolyl, 4-(2-aminoethyl)-2-thiazolyl, 2-amino-5,6-dimethyl-3pyrazinyl, 4-carbamoylpiperidino, furthermore, for example, 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3-methyl-5-tert.-butyl-2-thienyl, 5-chloro-2-thienyl, 5-phenyl -2- or -3-thienyl, 1-, 3-, 4- or 5-methyl-2-pyrryl, 1-methyl-4- or -5-nitro-2-pyrryl, 3,5-dimethyl-4-ethyl-2pyrryl, 4-methyl-5-pyrazolyl, 4- or 5-methyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl-2-pyridyl, 2-, 4-, 5-or 6-methyl-3-pyridyl, 2- or 3-methyl-4-pyridyl, 3-, 4-, 5- or 6-chloro-2-pyridyl, 2-, 4-, 5- or 6-chloro-3pyridyl, 2- or 3-chloro-4-pyridyl, 2,6-dichloropyridyl, 2-hydroxy-3-, -4-, -5- or -6-pyridyl (=1H-2-pyridon-3-, -4-, -5- or -6-yl), 5-phenyl-1H-2-pyridon-3-yl, 5-p-methoxyphenyl -1H-2-pyridon-3-yl, 2-methyl-3-hydroxy-4-hydroxymethyl -5-pyridyl, 2-hydroxy-4-amino-6-methyl-3-pyridyl, 3—N'-methylureido-1H-4-pyridon-5-yl, 5- or 6-methyl-4-pyrimidyl, 2,6-dihydroxy-4-pyrimidyl, 5-chloro-2-methyl-4-pyrimidyl, 2-methyl-4-amino-5-pyrimidyl, 3-methyl-2benzofuryl, 2-ethyl-3-benzofuryl, 7-methyl-2-benzothienyl, 1-, 2-, 4-, 5-, 6- or 7-methyl-3-indolyl, 1-methyl-5- or -6-benzimidazolyl, 1-ethyl-5- or -6-benzimidazolyl, or 3-, 4-, 5-, 6-, 7- or 8-hydroxy-2-quinolyl.

R is preferably A, in particular methyl, ethyl, propyl, isopropyl, butyl, isobutyl or tert.-butyl, furthermore preferably cyclopropyl, cyclopentyl, cyclohexyl, phenyl, benzyl or morpholino.

$R^1$ is preferably 2-, 3- or 4-pyridylmethyl, furthermore 1-, 2-, 3- or 4-piperidylmethyl. Accordingly, the NH—CHR$^1$—CO— group is preferably 2-, 3- or 4-Pya, furthermore 1-, 2-, 3- or 4-Pia.

$R^2$, $R^5$, $R^8$, $R^{11}$, $R^{12}$ and $R^{13}$ are preferably H or methyl, furthermore ethyl, propyl, isopropyl, butyl or isobutyl.

$R^3$ and $R^6$ are preferably cyclohexylmethyl, furthermore preferably A, in particular methyl, ethyl, propyl, isopropyl, butyl, isobutyl, sec.-butyl, pentyl, isopentyl (3-methylbutyl) or 2-methylbutyl, phenyl, benzyl, p-chlorobenzyl, 2-cyclohexylethyl, bicyclo[2,2,1]heptyl-2-methyl or 6,6-dimethylbicyclo[3,1,1]heptyl-2-methyl.

$R^4$ and $R^7$ are preferably (H, OH), furthermore preferably (H, NH$_2$).

$R^9$ is preferably H or Het, in particular pyridyl, 2-amino-5,6-dimethyl-3-pyrazinyl or 2-methyl-4-amino-5-pyrimidyl, furthermore also o-, m- or p-aminomethylphenyl.

$R^{10}$ is preferably H, methyl, ethyl, isobutyl or sec.-butyl, furthermore preferably propyl, butyl, cyclohexylmethyl or benzyl.

L is preferably CH. Q is preferably O or NH. D is preferably 0.

m, p, r and t are preferably 0, 1 or 2; n is preferably 1.

X is preferably H, POA, alkoxycarbonyl, such as ETOC, IPOC or BOC, CBZ, alkanoyl, such as acetyl, propionyl, butyryl or isobutyryl, cycloalkylcarbonyl, such as cyclopentylcarbonyl or cyclohexylcarbonyl, aroyl, such as benzoyl, arylalkanoyl, such as phenylacetyl, 2- or 3-phenylpropionyl, 4-phenylbutyryl, 2-benzyl-3-phenylpropionyl, PBB, 2-(2-phenylethyl) -4-phenylbutyryl, 2-(2-naphthylmethyl)-4-phenylbutyryl, 2- or 3-o-, -m- or -p-fluorophenylpropionyl, 2- or 3-o-, -m- or -p-chlorophenylpropionyl, cycloalkytalkanoyl, such as cyclohexylacetyl, 2- or 3-cyclohexylpropionyl, N-alkylcarbamoyl, such as ETNC or IPNC, or MC. Particularly preferred radicals X are BOC and MC, in addition ETOC, IPOC, ETNC, IPNC and PBB, furthermore H, POA, 4-phenylbutyryl, 2-benzyl-3-phenylpropionyl, 2-(2-phenylethyl)-4-phenylbuttyryl, 2-(2-naphthylmethyl)-4-phenylbutyryl and CBZ.

Z is preferably 1, but alternatively O or 2, in addition 3 or 4 amino acid radicals which are bonded together in a peptide fashion, in particular one of the groups Phe, Pro-Phe or His-Pro-Phe, furthermore preferably the groups Abu, Ada, Arg, Asn, Bia, Cal, Dab, Gln, Glu, His, Ile, N-(im) -methyl-His, Leu, tert.-Leu, Lys, Met, αNal, βNal, Nbg, Nle, Orn, N-Me-Phe, Pro, Ser, Thr, Tic, Trp, Tyr, Val, Ada-Phe, Ala-His, Ala-Phe, Phe-Abu, Phe-Ada, Phe-Ala, Phe-Arg, Phe-Asn, Phe-Bia, Phe-Cal, Phe-Dab, Phe-Gln, Phe-Glu, Phe-(N-im-Methyl-His), Phe-Ile, Phe-Leu, Phe-tert.-Leu, Phe-Lys, Phe-Met, Phe-o-Nal, Phe-βNal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-Ala, Pro-Ala-Phe, Pro-Phe-Ala, Pro-Phe-Phe, His-Pro-Ala, His-Pro-Ala-Phe, His-Pro-Phe-Ala, His-Pro-Phe-Phe, furthermorePro-Abu, Pro-Ada, Pro-Arg, Pro-Asn, Pro-Bia, Pro-Dab, Pro-Glu, Pro-His, Pro-Ile, Pro-Leu, Pro-tert.Leu, Pro-Lys, Pro-Met, Pro-Nbg, Pro-Nle, Pro-(N-Me-His), Pro-(N-Me-Phe), Pro-Orn, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Glu, Pro-Phe-(N-im-Methyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser, Pro-Thr, Pro-Tic, Pro-Trp, Pro-Tyr, Pro-Val, His-Pro-Abu, His-Pro-Ada, His-Pro-Arg, His-Pro-Asn, His-Pro-Bia, His-Pro-Dab, His-Pro-Glu, His-Pro-His, His-Pro-Ile, His-Pro-Leu, His-Pro-tert.-Leu, His-Pro-Lys, His-Pro-Met, His-Pro-Nbg, His-Pro-Nle, His-Pro-(N-Me-His), His-Pro-(N-Me-Phe), His-Pro-Orn, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Glu, His-Pro-Phe(N-im-Methyl-His), His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro, His-Pro-Ser,His-Pro-Thr, His-Pro-Tic, His-Pro-Trp, His-Pro-Tyr, His-Pro-Val.

E is preferably absent or is preferably Ile or Leu, furthermore preferably Abu, Cal, Met or Nle.

The groups W and W' are preferably —NH—CHR³—CHOH—CH₂—CO— or —NH—CHR⁶—CHOH—CH₂—CO—, in particular —NH—CH(cyclohexylmethyl)—CHOH—CH₂—CO— ("AHCP", derived from 4-amino-3-hydroxy-5-cyclohexylpentanoic acid), furthermore —NH—CH(—CH₂CH₂-cyclohexyl)—CHOH—CH₂—CO— ("AHCH"; derived from 4-amino-3-hydroxy-6-cyclohexylhexanoic acid), —NH—CH—(isobutyl)—CHOH—CH₂—CO— ("Sta"; derived from statine) or —NH—C-H(benzyl)—CHOH—CH₂—CO—("AHPP"; derived from 4-amino-3-hydroxy-5-phenylpentanoic acid). The groups W and W' are furthermore preferably —NH—CHR³—CH(NH₂)—CH₂—CO— or —NH—CHR⁶—CH(NH₂)—CH₂—CO—, in particular —NH—CH(cyclohexylmethyl) —CH(NH₂)—CH₂—CO— ("DACP"; derived from 3,4-diamino-5-cyclohexylpentanoic acid), —NH—CH(CH₂CH₂-cyclohexyl) —CH(NH₂)—CH₂—CO— ("DACH"; derived from 3,4-diamino-6-cyclohexylhexanoic acid), —NH—CH(isobutyl)—CH(NH₂)—CH₂—CO— ("DAMH"; derived from 3,4-diamino-6-methylheptanoic acid) or —NH—CH(benzyl)—CH(NH₂)—CH₂—CO— ("DAPP"; derived from 3,4-diamino-5-phenylpentanoic acid).

The groups W and W' each have at least one chiral center. The compounds of the formula I can thus exist in various - optically inactive or optically active—forms. The formula I covers all these forms. If W is —NH—CHR³—CR⁴CH⁴—CH₂—CO— where $R^4$=(H, OH) or (H, NH₂) or if W' is —NH—CHR⁶—CR⁷—CH₂—CO— where $R^7$=(H, OH) or (H, NH₂), the S-hydroxy-4S-amino enantiomers and 3S,4S-diamino enantiomers respectively are preferred. Unless otherwise stated in the designation of individual substances, the abbreviations AHCP, AHCH, Sta, AHPP, DACP, DACH, DAMH and DAPP always refer to the 3S,4S forms.

Y is preferably OH, OMe, OEt, NH₂, pyridyl-methylamino (in particular 3-pyridyl-methyl-amino), 4-amino-2-methyl -5-pyrimidyl-methyl-amino or 2-amino-5,6-dimethyl-3-pyrazinyl-methyl-amino. The preferred number of substituents in the substituted cyclic groups mentioned above is 1-3, in particular 1-2.

Accordingly, the invention relates, in particular, to those compounds of the formula I in which at least one of the radicals mentioned has one of the preferred meanings defined above. Some preferred groups of compounds may be expressed through the following part formulae Ia to Ic, which correspond to the formula I, but in which:

In Ia
X is H, ETOC, IPOC, BOC, CBZ, ETNC, IPNC or MC,
Z is Phe, Cal, αNal or βNal,
$R^2$ and $R^5$ are H,
$R^3$ is isobutyl, cyclohexylmethyl, 2-cyclohexylethyl or benzyl,
n is 1,
E is Ile, Leu or Nle, and
W' is missing or is AHCP, AHCH, Sta, AHPP, DACP, DACH, DAMH or DAPP;

In Ib
X is H, ETOC, IPOC, BOC, ETNC, IPNC or MC,
Z is Phe, Cal, αNal or BNal,
$R^1$ is Pya,
$R^2$ and $R^5$ are H,
$R^3$ is cyclohexylmethyl,
$R^4$ is (H, OH),
n is 1,
E is Ile, Leu or Nle, and
W' is missing or is DAMH;

In Ic
X is BOC
Z is Phe,
$R^1$ is 3-Pya,
$R^2$ and $R^5$ are each H,
$R^3$ is cyclohexylmethyl,
$R^4$ is (H, OH),
n is 1, and
E is Ile, and W' is missing.

Furthermore preferred compounds of the formulae I' and Ia' to Ic' are those which correspond to the formulae I and Ia to Ic, but wherein
Y is OH, OMe, OEt, NH₂, NH—CH₂—(3-pyridyl), NH—CH₂—(4-amino-2-methyl-5-pyrimidyl) or NH—CH₂-(2-amino-5,6-dimethyl-3-pyrazinyl).

The invention furthermore relates to a process for the preparation of the peptide of the formula I and its salts, characterized in that it is liberated from one of its functional derivatives by treatment with a solvolysing or hydrogenolyzing agent, or in that a compound which corresponds to the formula I, but which contains one or more additional C—C and/or C—N and/or C—O bonds and or O atoms in place of H atoms, is reduced, or in that a carboxylic acid of the formula II X—G¹—OH    II
in which G¹ is
(a) —Z¹—
(b) —Z—,
(c) —Z—NH—CHR¹—CO—,
(d) —Z—NH—CHR¹—CO—W—,
(e) —Z—NH—CHR¹—CO—W—E¹—,
(f) —Z—NH—CHR¹—CO—W—E—
(g) —Z—NH—CHR¹—CO—W—E—W'—
and
W is —NR²—CHR³—CR⁴—(CHR⁵)ₙ—CO—
is reacted with an amino compound of the formula III
H—G²    III
in which G² is
(a) —Z²—NH—CHR¹—CO—W—E—W'—Y,
(b) —NH—CHR¹—CO—W—E—W'—Y,
(c) —W—E—W'—Y,
(d) —E—W'—Y,
(e) —E²—W'—Y,
(f) —W'—Y,
(g) —Y (in which Q is NH),
E¹ + E² together are E and
Z¹ + Z² together are Z, and in that, if appropriate, in a compound of the formula I, a functionally modified amino and/or hydroxyl group is liberated by treatment with solvolyzing or hydrogenolyzing agents and/or for the preparation of a compound of the formula (I) in which $R^4$ and/or $R^7$ are (H, OH) or (H, NH$_2$), an aminoketo acid of the formula I in which $R^4$ and/or $R^7$ are O is reduced or reductively aminated, and/or a radical Y is converted into another radical Y through treatment with esterifying, solvolyzing or amidating agents and/or a compound of the formula I is converted into one of its salts through treatment with an acid.

The compounds of the formula I and also the starting materials for their preparation are, in addition, prepared by methods which are known per se, as described in the literature (for example, in the standard works such as Houben-Weyl, Methoden der organischen Chemie [Methods of Organic Chemistry], Georg-Thieme-Verlag, Stuttgart; furthermore, EP-A-45,665, EP-A-77,028, EP-A-77,029, EP-A81,783 and EP-A-152,255), to be precise under reaction conditions which are known and suitable for the reactions mentioned. Use can also be made here of variants which are known per se; but not described here in greater detail.

If desired, the starting materials can also be formed in situ, so that they are not isolated from the reaction mixture, but instead further reacted immediately to form the compounds of the formula I.

The compounds of the formula I can be obtained by liberating them from their functional derivatives through solvolysis, in particular hydrolysis, or through hydrogenolysis.

Preferred starting materials for the solvolysis or y hydrogenolysis are those which contain appropriately protected amino and/or hydroxyl groups in place of one or more free-amino and/or hydroxyl groups, preferably those which carry an amino-protecting group in place of an H atom which is bonded to an N atom, for example those which correspond to the formula I, but contain an N(im)-$R^{14}$-His group (in which $R^{14}$ is an amino-protecting group, for example BOM or DNP) in place of a His group, or those of the formula X—Z—CHR$^1$—CO—NR$^2$—CHR$^3$—CH(NHR$^{1-4}$)—(CHR$^5$)$_n$—CO—E—W'—Y.

Furthermore, preferred starting materials are those which carry a hydroxyl-protecting group in place of the H atom of a hydroxyl group, for example those of the formula X—Z—NH—CHR$^1$—CO—NR$^2$—CHR$^3$—CHOR$^{15}$—(CHR$^5$)$_n$—CO—E—W'—Y in which $R^{15}$ is a hydroxyl-protecting group.

It is also possible for several—identical or different—protected amino and/or hydroxyl groups to be present in the molecule of the starting material. If the protecting groups present are different from one another, they may in many cases be removed selectively.

The term "amino-protecting group" is generally known and relates to groups which are suitable for protecting (blocking) an amino group against chemical reactions, but which can easily be removed after the chemical reaction desired has been carried out elsewhere in the molecule. Typical such groups are, in particular, unsubstituted or substituted acyl, aryl (for example DNP), aralkoxymethyl (for example BOM) or aralkyl (for example benzyl, 4-nitrobenzyl and triphenylmethyl) groups. Since the amino-protecting groups are removed after the reaction (or reaction sequence) desired, their type and size are, in addition, not critical; however, preferred groups are those having 1-20, in particular 1-8, carbon atoms. In connection with the present process, the term "acyl group" should be taken in the broadest sense. It includes acyl groups which are derived from aliphatic, araliphatic, aromatic or heterocyclic carboxylic acids or sulfonic acids and, in particular, alkoxycarbonyl, aryloxycarbonyl and, above all, aralkoxycarbonyl groups. Examples of such acyl aralkanoyl, such as phenylacetyl; aroyl, such as benzoyl or toluyl; aryloxyalkanoyl, such as POA; alkoxycarbonyl, such as methoxycarbonyl, ethoxycarbonyl, 2,2,2-trichloroethoxycarbonyl, BOC or 2-iodoethoxycarbonyl; and aralkyloxycarbonyl, such as CBZ ("carbobenzoxy"), 4-methoxybenzyloxycarbonyl or FMOC. Preferred amino-protecting groups are DNP and BOM, furthermore CBZ, FMOC, benzyl and acetyl.

The term "hydroxyl-protecting group" is likewise generally known and relates to groups which are suitable for protecting a hydroxyl group against chemical reactions, but which can easily be removed after the chemical reaction desired has been carried out elsewhere in the molecule. Typical such groups are the abovementioned unsubstituted or substituted aryl, aralkyl or acyl groups, furthermore also alkyl groups. The nature and size of the hydroxyl-protecting groups is not critical since they are removed again after the chemical reaction or reaction sequence desired; preferred groups are those having 1-20, in particular 1-10, carbon atoms. Examples of hydroxyl-protecting groups are, inter alia, benzyl, p-nitrobenzoyl, p-toluenesulfonyl and acetyl, benzyl and acetyl being particularly preferred.

The functional derivatives, to be used as starting materials, of compounds of the formula I can be prepared by conventional methods of amino acid and peptide synthesis, as described, for example, in the standard works and patent applications mentioned.

The compounds of the formula I are liberated from their functional derivatives—depending on the protecting group used—for example, using strong acids, preferably using trifluoroacetic acid or perchloric acid, but alternatively other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but not always necessary. Suitable inert solvents are preferably organic, for example carboxylic acids, such as acetic acid, ethers, such as tetrahydrofuran or dioxane, amides, such as dimethylformamide (DMF), halogenated hydrocarbons, such as dichloromethane, furthermore also alcohols, such as methanol, ethanol or isopropanol, and also water. Mixtures of the above-mentioned solvents are furthermore suitable. Trifluoroacetic acid is preferably used in excess without addition of a further solvent, and perchloric acid is preferably used in the form of a mixture of acetic acid and 70% perchloric acid in the ratio 9:1. The reaction temperatures for the cleavage are preferably between about 0° and about 50°, preferably between 15° and 30° (room temperature).

The BOC group can preferably be removed, for example, using 40% trifluoroacetic acid in methylene chloride or using about 3 to 5 N HCl in dioxane at 15°-30°, and the FMOC group using an approximately 5 to 20% solution of dimethylamine, diethylamine or piperidine in DMF at 15°-30° The DNP group is also removed, for example, using an approximately 3 to 10% solution of 2-mercaptoethanol in DMF/water at 15°-30°.

Protecting groups which can be removed hydrogenolytically (for example BOM, CBZ or benzyl) can be removed, for example, through treatment with hydrogen in the presence of a catalyst (for example a noble-metal catalyst such as palladium, preferably on a support such as charcoal). Suitable solvents here are the abovementioned, in particular, for example, alcohols, such as methanol or ethanol, or amides, such as DMF. The hydrogenolysis is generally carried out at temperatures between about 0° and 100° and pressures between about 1 and 200 bar, preferably at 20°-30° and 1-10 bar. Hydrogenolysis of the CBZ group is readily achieved, for example, on 5 to 10% Pd/C in methanol at 20°-30°.

The compounds of the formula I can also be obtained by reducing corresponding compounds which contain one or more additional C—C and/or C—N and/or C—O bonds and/or 0 atoms in place of H atoms.

Thus, for example, amino compounds of the formula I which contain a substituent Ar=aminophenyl can be obtained by reducing the corresponding nitro compounds, for example by catalytic hydrogenation under the conditions mentioned above for hydrogenolysis.

Compounds of the formula I can also be obtained through direct peptide synthesis from a carboxylic acid (formula II) and an amine component (formula III). Suitable carboxylic acid components are, for example, those of the part formulae X—Z—OH, X—Z—N-H—CHR$^1$—COOH, X—Z—NH—CR$^1$—CO—W—OH, X—Z—NH—CHR$^1$—CO—W—E—OH or X—Z—NH—CR$^1$—CO—W—E—W'—OH, and suitable amine components are those of the part formulae H$_2$N—CHR$^1$—CO—W—E—W'—Y, H—W—E—W'—Y, H—E—W'—Y, H-W'—Y or H—Y (in which Q is NH, i.e. H$_2$N—C$_r$H$_{2r}$—R$^9$). However, the peptide bond can also be linked within the group Z or E; in this case, a carboxylic acid of the formula X—Z$^1$—OH or X—Z—NH—CR$^1$—CO—W—E$^1$—OH is reacted with an amino compound of the formula H—Z$^2$—NH—CR$^1$—CO—W—E—W'—Y or H—E$^2$'—W'—Y where Z$^1$+Z$^2$=Z and E$^1$+E$^2$=E respectively. This reaction is preferably carried out by conventional methods of peptide synthesis, as described, for example, in Houben-Weyl, loc. cit., volume 15/II, pages 1 to 806 (1974).

The reaction is preferably carried out in the presence of a dehydrating agent, for example a carbodiimide such as DCCI or dimethylaminopropylethylcarbodiimide, furthermore propanephosphoric anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, or a nitrile such as acetonitrile, at temperatures between about −10 and 40, preferably between 0° and 30°.

In place of II or III, suitable reactive derivatives of these substances may alternatively be employed in the reaction, for example those in which reactive groups are temporarily blocked by protecting groups. The amino acid derivatives III can be used, for example, in the form of their activated esters, which are preferably formed in situ, for example by adding HOBt or N-hydroxysuccinimide.

The majority of the starting materials of the formulae II and III are known. If they are unknown, they can be prepared by known methods, for example the abovementioned methods of peptide synthesis and removal of protecting groups.

If desired, a functionally derived amino and/or hydroxyl group in a compound of the formula I can be liberated through solvolysis or hydrogenolysis by one of the methods described above.

Thus, in particular, a compound of the formula I in which X is other than H can be converted into a compound of the formula I (X=H), preferably through hydrogenolysis if X is CBZ, otherwise through selective solvolysis. If X is BOC, the BOC group can be removed, for example, using HCl in dioxane at room temperature.

In addition, for example, keto compounds of the formula I (R$^4$ and/or R$^7$=0) can be reduced to form compounds of the formula I (R$^4$ and/or R$^7$=H, OH), for example using a complex metal hydride, such as NaBH$_4$, which does not simultaneously reduce the peptide carbonyl groups in an inert solvent, such as methanol, at temperatures between about −10° and +30°.

Keto compounds of the formula I (R$^4$ and/or R$^7$=0) can also be converted into compounds of the formula I (R$^4$ and/or R$^7$=H, NH$_2$) by reductive amination. The reductive amination can be carried out in one or several steps. Thus, for example, the keto compound can be treated with ammonium salts, for example ammonium acetate, NaCNBH$_3$, preferably in an inert solvent, for example an alcohol such as methanol, at temperatures between about 0° and 50° C., in particular between 15° and 30°. In addition, it is possible to initially convert the keto compound into the oxime in a conventional fashion using hydroxylamine, and to reduce the oxime to the amine, for example by catalytic hydrogenation on Raney nickel.

It is furthermore possible to convert a radical Y into another radical Y through treatment with esterifying, solvolyzing or amidating agents. Thus, an acid can be esterified, for example, with the aid of an alcohol of the formula A—OH or a diazoalkane, for example diazomethane, or an ester can be saponified into the corresponding acid, for example using aqueous-dioxanic sodium hydroxide solution at room temperature. Furthermore, for example, an ester can be converted into the corresponding amide through treatment with ammonia or with an amine of the formula A—NH$_2$ or A$_2$NH.

A base of the formula I can be converted into the pertinent acid-addition salt using an acid. Suitable acids for this reaction are, in particular, those which give physiologically acceptable salts. Thus, inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane or ethanesulfonic acid, ethanedisulfonic acid, 2-hydroxyethanesulfonic acid, benzenesulfonic acid, p-toluenesulfonic acid, naphthalene-mono- and disulfonic acids, and laurylsulfuric acid may be used. Salts with physiologically unacceptable acids, for example picrates, can be used for isolating and/or purifying the compounds of the formula I.

The novel compounds of the formula I and their physiologically acceptable salts can be used for the preparation of pharmaceutical preparations by converting them into a suitable dosage form together with at least one excipient or adjuvant and, if desired, together with one or more further active ingredients. The preparations thus obtained can be employed as medicaments in human or veterinary medicine. Suitable excipients are organic or inorganic substances which are suitable for enteral (for example oral or rectal) or parenteral administration or for administration in the form of an inhalation spray and which do not react with the novel compounds, for example water, vegetable oils, benzyl alcohols, polyethylene glycols, glycerol triacetate and other fatty acid glycerides, gelatin, soybean lecithin, carbohydrates, such as lactose or starch, magnesium stearate, talc or cellulose. For oral administration, tablets, coated tablets, capsules, syrups, juices or drops are particularly used; lacquered tablets and capsules having gastric juice-resistant coatings or capsule shells are of particular interest. Rectal administration is effected by suppositories, and parenteral administration by solutions, preferably oily or aqueous solutions, furthermore suspensions, emulsions or implants. For administration as inhalation spray, sprays which contain the active ingredient either dissolved or suspended in a propellant gas mixture (for example fluorochlorohydrocarbons) can be used. The active ingredient is preferably used here in micronized form, where one or more additional physiologically acceptable solvents may be present, for example ethanol. Inhalation solutions can be administered with the aid of conventional inhalers. The novel compounds can also be lyophilized, and the lyophilizates obtained can be used, for example, for the preparation of injection preparations. The preparations specified can be sterilized and/or contain adjuvants, such as preservatives, stabilizers and/or wetting agents, emulsifiers, salts for influencing the osmotic pressure, buffers, colorants and/or fragrances. If desired, they can also contain one or more further active ingredients, for example one or more vitamins.

The substances according to the invention are generally administered analogously to other known, commercially available peptides, but, in particular, analogously to the compounds described in EP-A-77,028, preferably in dosages between about 100 mg and 30 g, in particular between 500 mg and 5 g, per dosage unit. The daily dosage is preferably between about 2 and 600 mg/kg of body weight. However, the specific dose for each particular patient depends on a very wide variety of factors, for example on the activity of the specific compound employed, on the age, body weight, general health, sex, on the diet, on the point in time and method of administration, on the rate of excretion, medicament combination and severity of the respective disorder to which the therapy applies Parenteral administration is preferred.

Renin-dependent hypertension and hyperaldosteronism can be effectively treated by administration of dosages between about 1 and 300, preferably 5 and 50,mg/kg of body weight. For diagnostic purposes, the new amino acid derivatives can be administered in a single dose of from 0.1 to 10 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

In the following examples, "conventional work-up" denotes: if necessary, water is added to the mixture, which is neutralized and extracted with ether or dichloromethane, the phases are separated, the organic phase is dried over sodium sulfate, filtered and evaporated, and the product is purified by chromatography on silica gel and/or crystallization.

EXAMPLE 1

A mixture of 1 g of N-[3S-hydroxy-4S-(N-tert.-butoxy -carbonyl-L-phenylalanyl-L-(N-imi-2,4-dinitrophenylhistidyl) -L-(3-pyridyl)-alanyl-amino)-5-cyclohexyl-pentanoyl]-isoleucine ["BOC-Phe-(imi-DNP-His)-(3-Pya)-AHCP-IleOH"; obtainable through reaction of BOC-(3-Pya)-OH with H-AHCP-Ile-OMe in the presence of N-methylmorpholine/HOBt/DCCI to form BOC-(3-Pya)-AHCP-Ile-OMe, removal of the BOC, group, reaction with BOC-Phe-(imi-DNP-His)-OH to form BOC-Phe -(imi-DNP-His)-(3-Pya)-AHCP-Ile-OMe and saponification], 2 g of 2-mercaptoethanol, 20 ml of DMF and 20 ml of water is adjusted to pH 8 using aqueous $Na_2CO_3$ solution with stirring at 20°, and stirred at 20° for 2 hours. After conventional work-up, N-[3S-hydroxy-4S-(N-tert.-butoxycarbonyl -L-phenylalanyl-L-histidyl-L-(3-pyridyl)-alanyl-amino)-5-cyclohexylpentanoyl]-isoleucine ("BOC-Phe-His-(3-Pya)-AHCP-Ile-OH").

The following are obtained analogously through cleavageage of the appropriate (imi-DNP-His) derivatives:
BOC-Phe-His-(2-Pya)-AHCP-Ile-OH
BOC-Phe-His-(4-Pya)-AHCP-Ile-OH
BOC-Phe-His-(2-Pia)-AHCP-Ile-OH
BOC-Phe-His-(3-Pia)-AHCP-Ile-OH
BOC-Phe-His-(4-Pia)-AHCP-Ile-OH.

EXAMPLE 2

1 g of BOC-Phe-(imi-BOM-His)-(3-Pya)-AHCP-Ile-OMe [obtainable from BOC-Phe-(imi-BOM-His)-OH and H-(3-Pya)-AHCP -Ile-OMe] is dissolved in 10 ml of methanol, hydrogenated for 3 hours on 0.5 g of 10% Pd/C at 20° and I bar, filtered and evaporated, and BOC-Phe-His-(3-Pya)-AHCP-Ile-OMe is obtained after conventional work-up.

EXAMPLE 3

1 g of methyl 3S—CBZ-amino-4S-[BOC-Phe-(3-Pya)-AHCP-Ile -amino]-6-methylheptanoate ["BOC-Phe-(3-Pya)-AHCP-Ile-(CBZ-DAMH)-OMe"; melting point 210°-214°; obtainable through reaction of BOC-Phe-(3-Pya)-AHCP-OH with methyl 3S—CBZ-amino -4S-(H-Ile-amino)-6-methylheptanoate hydrochloride]is dissolved in 10 ml of ethanol, hydrogenated on 0.5 g of 10% Pd/C at 20° and 1 bar until cessation, and evaporated, and BOC-Phe-(3-Pya)-AHCP-Ile-DAMH-OMe is obtained after chromatographic purification; melting point 203°-205°.

The following are obtained analogously through cleavage of the appropriate CBZ derivatives:
BOC-Phe-(3-Pya)-AHCP-Ile-DACP-OMe
BOC-Phe-(3-Pya)-AHCP-Ile-DACH-OMe BOC-Phe-(3-Pya)-AHCP-Ile-DAPP-OMe.

EXAMPLE 4

Analogously to Example 3, 3S-hydroxy-4S-[2-BOC-Phe-amino -3-(1—CBZ-3-piperidyl)-propionylamino]-5-cyclohexylpentanoyl-isoleucine methyl ester ["BOC-Phe-(3—CBZ-Pia)-AHCP-Ile-OMe"; obtainable through hydrogenation of BOC-(3-Pya)-OH to form BOC-(3-Pia)-OH, reaction with CBZ—Cl to form BOC-(3—CBZ-Pia)-OH, reaction with H-AHCP-Ile-OMe to form BOC-(3—CBZ-Pia)-AHCP-Ile-OMe, removal of the BOC group to form H-(3—CBZ-Pia)-AHCP-Ile-OMe and reaction with BOC-Phe-OH]is hydrogenolyzed to form BOC-Phe-(3-Pia)-AHCP-Ile-OMe.

The following are obtained analogously:
BOC-Phe-(2-Pia)-AHCP-Ile-OMe
BOC-Phe-(3-Pia)-AHCP-Ile-OMe.

EXAMPLE 5

Analogously to Example 3, methyl 3S-(CBZ-amino)-4S -[BOC-Phe-(3—CBZ-Pia)-AHCP-Ile-amino]-6-methylheptanoate [obtainable through saponification of BOC-Phe-(3—CBZ-Pia)-AHCP-OMe to form the free acid and reaction with methyl 3S-(CBZ-amino) -4S-Ile-amino-6-methylheptanoate] is hydrogenolyzed to form 80C-Phe-(3-Pia)-AHCP-Ile-DAMH-OMe.

EXAMPLE 6

A solution of 1 g of BOC-Phe-(3-Pya)-AHCP-Ile-(N-2-p-nitrophenyl-ethyl-amide) [obtainable from BOC-Phe-(3-Pya) -AHCP-Ile-OH and p-nitrobenzylamine] in 50 ml of methanol is hydrogenated on 1 g of 5% Pd/C at 20° and 1 bar until the calculated amount of hydrogen has been taken up. The reaction mixture is filtered and evaporated, and BOC-Phe(3-Pya) -AHCP-Ile-(N-2-p-aminophenyl-ethyl-amide) is obtained.

EXAMPLE 7

1.01 g of N-methylmorpholine is added to a solution of 5.96 g of N-[3S-hydroxy-4S-(2S-amino-3-(3-pyridyl)-propionylamino) -5-cyclohexylpentanoyl]-isoleucine-(N-4-amino-2-methyl -5-pyrimidinyl-methyl-amide) ["H-(3-Pya)-AHCP-Ile-(N-4-amino-2-methyl-5-pyrimidinyl-methyl-amide)"; obtainable through removal of the BOC group from BOC-AHCP-Ile-(N-4-amino -2-methyl-5-pyrimidinyl-methyl-amide (melting point from 225°, decomposition) using HCl/dioxane, reaction with BOC-(3-Pya)-OH to form BOC-(3-Pya)-AHCP-Ile-(N-4-amino-2-methyl -5-pyrimidinyl-methyl-amide (melting point 165°-172°) and re-removing the BOC group] in 60 ml of dichloromethane. 2.65 g of BOC-Phe-OH, 1.35 g of HOBt and a solution of 2.06 g of DCCI in 50 ml of dichloromethane are added with stirring, the mixture is stirred for 14 hours at 2°-6°, the precipitated dicyclohexylurea is filtered off, and the filtrate is evaporated. After conventional work-up, BOC-Phe -(3-Pya)-AHCP-Ile-(N-4-amino-2-methyl-5-pyrimidinylmethyl-amide), melting point 185°-193° is obtained.

BOC-Phe-(3-Pya)-AHCP-Ile-(N-2-amino-5,6-dimethyl-3-pyrazinyl-methyl-amide, melting point 192°14 199°, is obtained analogously from H-(3-Pya)-AHCP-Ile-(N-2-amino-5,6-dimethyl-3-pyrazinyl-methyl-amide) [obtainable from BOC-AHCP-Ile-(N-2-amino-5,6-dimethyl-3-pyrazinyl -methyl-amide (melting point 175°) via BOC-(3-Pya)-AHCP-Ile-(N-2-amino-5,6-dimethyl-3-pyrazinyl-methyl-amide (melting point 175°-185°)].

EXAMPLE 8

BOC-Pro-Phe-(3-Pya)-AHCP-Ile-OMe is obtained analogously to Example 7 from BOC-Pro-OH and H-Phe-(3-Pya)-AHCP-Ile-OMe.

EXAMPLE 9

BOC-Phe-(3-Pya)-ACHP-Ile-(N-4-amino-2-methyl-5-pyrimidinyl-methyl-amide), melting point 185°-193°, is obtained analogously to Example 7 from BOC-Phe-(3-Pya)-OH and H-AHCP-Ile -(N-4-amino-2-methyl-5-pyrimidinyl-methyl-amide). The following are obtained analogously using H-AHCP-Ile-OMe:
BOC-Phe-(2-Pya)-AHCP-Ile-OMe
BOC-Phe-(3-Pya)-AHCP-Ile-OMe
BOC-Phe-(4-Pya)-AHCP-Ile-OMe
BOC-Phe-(2-Pia)-AHCP-Ile-OMe
BOC-Phe-(3-Pia)-AHCP-Ile-OMe
BOC-Phe-(4-Pia)-AHCP-Ile-OMe
ETOC-Phe-(3-Pya)-AHCP-Ile-OMe
IPOC-Phe-(3-Pya)-AHCP-Ile-OMe
CBZ-Phe-(3-Pya)-AHCP-Ile-OMe
ETNC-Phe-(3-Pya)-AHCP-Ile-OMe
IPNC-Phe-(3-Pya)-AHCP-Ile-OMe
MC-Phe-(3-Pya)-AHCP-Ile-OMe
POA-Phe-(3-Pya)-AHCP-Ile-OMe
FMOC-Phe-(3-Pya)-AHCP-Ile-OMe.

The corresponding ethyl esters are obtained analogously using H-AHCP-Ile-OEt.

EXAMPLE 10

4S-[BOC-Phe-(3-Pya)-AHCP-Ile-amino]-5S-isobutylpyrrolidone is obtained analogously to Example 7 from BOC-Phe -(3-Pya)-AHCP-OH and 4S-(H-Ile-amino)-5S-isobutyl-pyrrolidone (preparable from H-Ile-OH and 4S-amino-5S-isobutylpyrrolidone).

The following are obtained analogously:
BOC-Phe-(3-Pya)-AHCP-Ile-NH , m.p. 221°-222°
BOC-Phe-(3-Pya)-AHCP-Ile-(N-3-pyridyl-methyl-amide)m.p.164°-174°
BOC-Phe-(3-Pya)-AHCP-Ile-(N-2-amino-5,6-dimethyl-3-pyrazinyl-methy-amide),m.p. 192-199
BOC-Phe-(3-Pya)-AHCP-Ile-(N-4-amino-2-methyl-5-pyrimidinyl-methyl-amide) ,m.p.185°-193°
BOC-Phe-(3-Pya)-AHCP-Ile-(N-2-hydroxy-4,6-dimethyl-3-pyridyl-methyl-amide)
BOC-Phe-(3-Pya)-AHCP-Ile-(N-5-tetrapolyl-methyl-amide)
IPOC-Phe-(3-Pya)-AHCP-Ile-NH
IPOC-Phe-(3-Pya)-AHCP-Ile-(N-3-pyridyl-methyl-amide)
IPOC-Phe-(3-Pya)-AHCP-Ile-(N-2-amino-5,6-dimethyl-3-pyrazinyl-methyl-amide)
IPOC-Phe-(3-Pya)-AHCP-Ile-(N-4-amino-2 methyl-5-pyrimidinyl-methyl-amide)
IPNC-Phe-(3-Pya)-AHCP-Ile-NH
IPNC-Phe-(3-Pya)-AHCP-Ile-(N-3-pyridyl--methyl-amide)
IPNC-Phe-(3-Pya)-AHCP-Ile-(N-2-amino-5,6-dimethyl-3-pyrazinyl-methyl-amide)
IPNC-Phe-(3-Pya)-AHCP-Ile-(N-4-amino-2-methyl-5-pyrimidinyl-methyl-amide)
MC-Phe-(3-Pya)-AHCP-Ile-NH
MC-Phe-(3-Pya)-AHCP-Ile-(N-3-pyridyl-methyl-amide)

MC-Phe-(3-Pya)-AHCP-Ile-(N-2-amino-5,6-dimethyl-5-pyrazinyl-methyl-amide)
MC-Phe-(3-Pya)-AHCP-Ile-(N-4-amino-2-methyl-5-pyrimidinyl-methyl-amide)
BOC—Cal-(3-Pya)-AHCP-Ile-NH
BOC—Cal-(3-Pya)-AHCP-Ile-(N-3-pyridyl-methyl-amide)
BOC—Cal-(3-Pya)-AHCP-Ile-(N-2-amino-5,6-dimethyl-3-pyrazinyl--methyl-amide)
BOC—Cal-(3-Pya)-AHCP-Ile-(N-4-amino-2-methyl-5-pyrimidinyl-methyl-amide)
BOC-αNal-(3-Pya)-AHCP-Ile-NH$_2$
BOC-αNal-(3-Pya)-AHCP-Ile-(N-3-pyridyl-methyl-amide)
BOC-αNal-(3-Pya)-AHCP-Ile-(N-2-amino-5,6-dimethyl-3-pyrazinyl-methyl-amide)
BOC-αNal-(3-Pya)-AHCP-Ile-(N-4-amino-2-methyl-5-pyrimidinyl-methyl-amide)
BOC—Nal-(3-Pya)-AHCP-Ile-NH$_2$
BOC—Nal-(3-Pya) TM AHCP-Ile-(N-3-pyridyl-methyl-amide)
BOC—Nal-(3-Pya)-AHCP-Ile-(N-2-amino-5,6-dimethyl-3-pyrazinyl-methyl-amide)
BOC-BNal-(3-Pya)-AHCP-Ile-(N-4-amino-2.methyl-5-pyrimidinyl-methyl-amide)
BOC-Phe-(3-Pya)-AHCP-Leu-NH$_2$
BOC-Phe-(3-Pya)-AHCP-Leu-(N-3-pyridyl-methyl-amide)
BOC-Phe-(3-Pya)-AHCP-Leu-(N-2-amino-5,6-dimethyl-3-pyrazinyl-methyl-amide)
BOC-Phe-(3-Pya)-AHCP-Leu-(N-4-amino-2-methyl-5-pyrimidinyl-methyl-amide)
BOC-Phe-(3-Pya)-AHCP-Nle-NH$_2$
BOC-Phe-(3-Pya)-AHCP-Nle-(N-3-pyridyl-methyl-amide)
BOC-Phe-(3-Pya)-AHCP-Nle-(N-2-amino-5,6-dimethyl-3-pyrazinyl-methyl-amide)
BOC-Phe-(3-Pya)-AHCP-Nle-(N-4-amino-2-methyl-5-pyrimidinyl-methyl-amide,
BOC-Phe-(3-Pya)-AHCH-Ile-NH$_2$
BOC-Phe-(3-Pya)-AHCH-Ile-(N-3-pyridyl-methyl-amide)
BOC-Phe-(3-Pya)-AHCH-Ile-(N-2-amino-5,6-dimethyl-3-pyrazinyl-methyl-amide)
BOC-Phe-(3-Pya)-AHCH-Ile-(N-4-amino-2-methyl-5-pyrimidinyl-methyl-amide)
BOC-Phe-(3-Pya)-Sta-Ile-NH$_2$
BOC-Phe-(3-Pya)-Sta-Ile-(N-3-pyridyl-methyl-amide)
BOC-Phe-(3-Pya)-Sta-Ile-(N-2-amino-5,6-dimethyl-3-pyrazinyl-methyl-amide)
BOC-Phe-(3-Pya)-Sta-Ile-(N-4-amino-2-methyl-5-pyrimidinyl-methyl-amide)
BOC-Phe-(3-Pya)-AHPP-Ile-NH$_2$
BOC-Phe-(3-Pya)-AHPP-Ile-(N-3-pyridyl-methyl-amide)
BOC-Phe-(3-Pya)-AHPP-Ile-(N-2-amino-5,6-dimethyl-3-pyrazinyl-methyl-amide)
BOC-Phe-(3-Pya)-AHPP-Ile-(N-4-amino-2-methyl-5-pyrimidinyl-methyl-amide).

EXAMPLE 11

BOC-Phe-(3-Pya)-AHCP-Ile-OMe is obtained analogously to Example 7 from BOC-Phe-(3-Pya)-AHCP-Ile-OH and H-Phe-OMe.

EXAMPLE 12

4R-[BOC-Phe-(3-Pya)-AHCP-Ile-amino]-5S-isobutylpyrrolidone is obtained analogously to Example 7 from BOC-Phe -(3-Pya)-AHCP-Ile-OH and 4R-amino-5S-isobutylpyrrolidone. 2-Thioxo-4S-[BOC-Phe-(3-Pya)-AHCP-Ile-amino]-5S-isobutylpyrrolidone is obtained analogously using 2-thioxo-4S-amino-5S-isobutylpyrrolidone.

The following are obtained analogously using m-bis-(aminomethyl)-benzene:
BOC-Phe-(3-Pya)-AHCP-Ile-(N-m-aminomethyl-benzyl-amide)
IPOC-Phe-(3-Pya)-AHCP-Ile-(N-m-aminomethyl-benzyl-amide)
IPNC-Phe-(3-Pya)-AHCP-Ile-(N-m-aminomethyl-benzyl-amide)
MC-Phe-(3-Pya)-AHCP-Ile-(N-m-aminomethyl-benzyl-amide)
BOC—Cal-Phe-(3-Pya)-AHCP-Ile-(N-m-aminomethyl-benzyl-amide)
Nal-Phe-(3-Pya)-AHCP-Ile-(N-m-aminomethyl-benzyl-amide)
BOC-BNal-Phe-(3-Pya)-AHCP-Ile-(N-m-aminomethyl-benzyl-amide)
BOC-Phe-(3-Pya)-AHCP-Leu-(N-m-aminomethyl-benzyl-amide)
BOC-Phe-(3-Pya)-AHCP-Nle-(N-m-aminomethyl-benzyl-amide).

EXAMPLE 13

BOC-Phe-(3-Pya)-AHCP-Ile-Sta-(N-2-amino-5,6-dimethyl-3-pyrazinyl-methyl-amide) is obtained analogously to Example 7 from BOC-Phe-(3-Pya)-AHCP-Ile-Sta-OH and 2-amino-3-aminomethyl-5,6-dimethyl-pyrazine.

EXAMPLE 14

A solution of 1 g of BOC-Phe-(3-Pya)-AHCP-Ile-OH in 20 ml of 4N HCl in dioxane is stirred at 20° for 30 minutes and then evaporated. H-Phe-(3-Pya)-AHCP-Ile-OH is obtained.

The following are obtained analogously through cleavage of the appropriate N-BOC derivatives:
H-Phe-(3-Pya)-AHCP-Ile-DAMH-OMe
H-Phe-(3-Pya)-AHCP-Ile-(N-3-pyridyl-methyl-amide
H-Phe-(3-Pya)-AHCP-Ile-(N-4-amino-2-methyl-5-pyrimidinylmethyl-amide
H-Phe-(3-Pya)-AHCP-Ile-(N-2-amino-5,6-dimethyl-3-pyrazinyl-methyl-amide.

EXAMPLE 15

1 g of CBZ-Phe-(3-Pya)-AHCP-Ile-OH is dissolved in 10 ml of ethanol, hydrogenated for 3 hours on 0.5 g of 10% Pd/C at 20° and 1 bar, filtered and evaporated, and H-Phe -(3-Pya)-AHCP-Ile-OH is obtained after chromatographic purification.

EXAMPLE 16

A solution of 1 g of N-[3-oxo-4S-(BOC-Phe-(3-Pya)-amino) -5-cyclohexyl-pentanoyl]-Ile-OH is hydrogenated on 0.1 g of 10% Pd/C at 20° and 1 bar until the calculated amount of hydrogen has been taken up. After filtration and evaporation, a mixture of N-[3R- and N-[3S-hydroxy-4S-(BOC-Phe-(3-Pya) -amino)-5-cyclohexyl-pentanoyl]-Ile-OH ["BOC-Phe-(3-Pya)-AHCP-Ile-OH"], which can be resolved by chromatography, is obtained.

19

EXAMPLE 17

70 mg of hydroxylamine hydrochloride are added to a solution of 721 mg of N-[3-oxo-4S-(2S-(N-tert.-butoxycarbonyl-L-phenylalanyl-amino) -3-(3-pyridyl)-propionylamino) -5-cyclohexylpentanoyl]-isoleucine and 1.43 g of $Na_2CO_3.10 H_2O$ in 5 ml of methanol and 5 ml of water, and the mixture is stirred at 20° for 14 hours. The precipitated oxime is filtered off, dried, dissolved in 10 ml of methanol and hydrogenated on 0.5 g of Raney Ni at 20° and 5 bar. The catalyst is filtered off, the filtrate is evaporated, the mixture remaining is resolved on silica gel, and N-[3S-amino-4S-(2S-(N-tert.-butoxycarbonyl-L-phenylalanylamino) -3-(3-pyridyl)-propionylamino)-5-cyclohexylpentanoyl]isoleucine ["BOC-Phe-(3-Pya)-DACP-Ile-OH"] is obtained; in addition, the 3R-amino epimer is obtained.

EXAMPLE 18

A solution of 1 g of BOC-Phe-(3-Pya)-AHCP-Ile-OMe in 50 ml of dioxane and 5 ml of 2N aqueous sodium hydroxide solution is stirred at 20° for 5 hours, evaporated, taken up in water, neutralized with 1N hydrochloric acid and worked up as conventional (ethyl acetate), and BOC-Phe-(3-Pya) -AHCP-Ile-OH is obtained.

EXAMPLE 19

In analogy to Example 7, BOC-Pro-Phe-(3-Pya)-AHCP-Ile-$NH_2$, m.p. 158°–62° is obtained from BOC-Pro-OH and H-Phe-l3-Pya)-AHCP-Ile-$NH_2$.

The following are obtained analogously:
CBZ-Arg-Pro-Phe-(3-Pya)-AHCP-Ile-$NH_2$, m.p. 128°
[2R-benzyl-4-(2-oxopyrrolidino)-butyryl]-(3-Pya)-AMCP-Ile-$NH_2$, m.p. 90°–102'
[2S-benzyl-4-(2-oxopyrrolidino)-butyryl]-(3-Pya)-AHCP-Ile-$NH_2$, m.p. 80°–95°
MC-Phe-(3-Pia)-AHCP-Ile-(N-2-amino-5,6-dimethyl-3-pyrazinylmethyl-amide), m.p. 146°–150°.

The following examples concern pharmaceutical preparations.

EXAMPLE A

Injection Vials

A solution of 100 g of BOC-Phe-(3-Pya)-AHCP-Ile-(N-amino-2-methyl-5-pyrimidinyl-methylamide) and 5 g of disodium hydrogen phosphate in 3 liters of twice-distilled water is adjusted to pH 6.5 using 2N hydrochloric acid, filtered under sterile conditions, transferred into injection vials, lyophilized under sterile conditions and sealed under sterile conditions. Each injection vial contains 500 g of active ingredient.

EXAMPLE B

Suppositories

A mixture of 500 g of BOC-Phe-(3-Pya)-AHCP-Ile-DAMH-OMe is melted with 100 g of soybean lecithin and 1400 g of cocoa butter, poured into moulds and allowed to cool. Each suppository contains 500 g of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula $$X-Z-NH-CHR^1-CO-NR^2-CHR^3-CH(OH)-(CHR^5)_n-CO-E-W'-Y$$

wherein
X is tert.-butoxycarbonyl, benzyloxycarbonyl, 6-aminohexanoyl, 4-aminopiperidinocarbonyl or morpholinocarbonyl;
Z is Phe, Pro-Phe or Arg-Pro-Phe;
$R^1$ is $-CH_2$-3-pyridyl;
$R^2$ is H;
$R^3$ is $-CH_2$-cyclohexyl;
$R^5$ is H;
n is 1;
E is Ile;
W' is absent; and
Y is OH, $OCH_3$, $OC_2H_5$, $NH_2$, $NH-CH_2-$(3-pyridyl), $NH-CH_2$-(4-amino-2-methyl-5-pyrimidinyl) or $NH-CH_2$-(2-amino-5,6-dimethyl-3-pyrazinyl).

2. A peptide according to claim 1 wherein X is tert.-butoxy-carbonyl.

3. Methyl 3S-amino-4S-[4S-(BOC-Phe-(L-(3-pyridyl)alanyl)-amino)-3S-hydroxy -5-cyclohexyl-pentanoylamino-Ile-amino]-6-methylheptanoate, a compound of claim 1.

4. A pharmaceutical composition comprising a compound of claim 1 and a pharmaceutically acceptable carrier.

5. A pharmaceutical composition comprising about 100 mg to 30 g of a compound of claim 1 and a pharmaceutically acceptable carrier.

6. A pharmaceutical composition comprising about 500 mg to 5 g of a compound of claim 1 and a pharmaceutically acceptable carrier.

7. A method of treating renin-dependent hypertension comprising administering a compound of claim 1.

8. A method according to claim 7, comprising administering doses of said compound in an amount of about 1 to 300 mg/kg of body weight.

9. A method according to claim 7, comprising administering doses of said compound in an amount of about 5 to 50 mg/kg of body weight.

10. A method for treating renin-dependent hyperaldosteronism comprising administering a compound of claim 1.

11. A method according to claim 10, comprising administering doses of said compound in an amount of about 1 to 300 mg/kg of body weight.

12. A method according to claim 10, comprising administering doses of said compound in an amount of about 5 to 50 mg/kg of body weight.

13. A method of treating renin-dependent cardiac insufficiency comprising administering a compound of claim 1.

* * * * *